(12) United States Patent
Einarsson

(10) Patent No.: US 11,051,851 B2
(45) Date of Patent: Jul. 6, 2021

(54) VERESS-TYPE NEEDLES WITH ILLUMINATED GUIDANCE AND SAFETY FEATURES

(71) Applicant: Brigham and Women's Hospital, Inc., Boston, MA (US)

(72) Inventor: Jon I. Einarsson, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/780,938

(22) Filed: Feb. 4, 2020

(65) Prior Publication Data

US 2020/0170672 A1 Jun. 4, 2020

Related U.S. Application Data

(63) Continuation-in-part of application No. PCT/US2018/045380, filed on Aug. 6, 2018.
(Continued)

(51) Int. Cl.

| A61B 1/00 | (2006.01) |
| A61B 17/34 | (2006.01) |
| A61B 1/015 | (2006.01) |
| A61B 1/05 | (2006.01) |
| A61B 1/06 | (2006.01) |

(Continued)

(52) U.S. Cl.
CPC ...... *A61B 17/3474* (2013.01); *A61B 1/00096* (2013.01); *A61B 1/00101* (2013.01); *A61B 1/00154* (2013.01); *A61B 1/015* (2013.01); *A61B 1/05* (2013.01); *A61B 1/0676* (2013.01); *A61B 1/0684* (2013.01); *A61B 1/3132* (2013.01); *A61B 17/320016* (2013.01); *A61B 17/3423* (2013.01); *A61B 17/3478* (2013.01);
(Continued)

(58) Field of Classification Search
None
See application file for complete search history.

(56) References Cited

U.S. PATENT DOCUMENTS

| 4,254,762 A * | 3/1981 | Yoon | A61B 1/00135 600/114 |
| 5,169,397 A | 12/1992 | Sakashita et al. | |

(Continued)

FOREIGN PATENT DOCUMENTS

| GB | 2481727 A | 1/2012 |
| WO | 1995013751 A1 | 5/1995 |

(Continued)

OTHER PUBLICATIONS

International Search Report and Written Opinion dated Oct. 24, 2018 for corresponding International Patent Application PCT/US2018/045380.
(Continued)

*Primary Examiner* — Timothy J Neal
(74) *Attorney, Agent, or Firm* — Winthrop & Weinstine, P.A.

(57) ABSTRACT

The present disclosure provides devices and methods for insufflating abdomens of subjects under direct visualization. Such devices and methods, in some implementations, include features for cleaning the devices, and certain implementations of the methods permit procedures wherein it is not necessary to use a typical obturator to place a cannula, resulting in safer procedures.

4 Claims, 11 Drawing Sheets

Related U.S. Application Data

(60) Provisional application No. 62/541,644, filed on Aug. 4, 2017.

(51) Int. Cl.
*A61B 1/313* (2006.01)
*A61B 17/32* (2006.01)
*A61M 13/00* (2006.01)

(52) U.S. Cl.
CPC .............. *A61M 13/003* (2013.01); *A61B 2017/320044* (2013.01); *A61M 2210/1021* (2013.01)

(56) References Cited

U.S. PATENT DOCUMENTS

| | | | |
|---|---|---|---|
| 5,209,721 A | 5/1993 | Wilk | |
| 5,271,380 A | 12/1993 | Riek et al. | |
| 5,290,276 A * | 3/1994 | Sewell, Jr. | A61B 17/3476 600/104 |
| 5,383,859 A | 1/1995 | Sewell, Jr. | |
| 5,609,562 A * | 3/1997 | Kaali | A61B 1/042 600/104 |
| 5,697,888 A | 12/1997 | Kobayashi et al. | |
| 7,708,713 B2 | 5/2010 | Albrecht et al. | |
| 7,927,272 B2 | 4/2011 | Bayer et al. | |
| 8,128,590 B2 | 3/2012 | Albrecht et al. | |
| 8,267,952 B2 | 9/2012 | Kahle et al. | |
| 8,517,977 B2 | 8/2013 | Taylor et al. | |
| 8,838,206 B2 | 9/2014 | Mohajer | |
| 2005/0288622 A1 | 12/2005 | Albrecht et al. | |
| 2006/0276692 A1 * | 12/2006 | Kucklick | A61B 1/012 600/175 |
| 2007/0282253 A1 | 12/2007 | Sasaki | |
| 2008/0004634 A1 | 1/2008 | Farritor et al. | |
| 2008/0243162 A1 | 10/2008 | Shibata et al. | |
| 2009/0248036 A1 * | 10/2009 | Hoffman | A61B 1/045 606/130 |
| 2010/0168520 A1 | 7/2010 | Poll et al. | |
| 2010/0191260 A1 | 7/2010 | Mohajer | |
| 2010/0274081 A1 | 10/2010 | Okoniewski | |
| 2011/0313255 A1 | 12/2011 | Stanley et al. | |
| 2012/0197078 A1 * | 8/2012 | Stanley | A61B 1/05 600/109 |
| 2014/0275986 A1 | 9/2014 | Vertikov | |
| 2015/0282695 A1 | 10/2015 | Tay et al. | |
| 2017/0042573 A1 * | 2/2017 | Savvouras | A61B 1/00154 |
| 2017/0173275 A1 | 6/2017 | Anderson et al. | |

FOREIGN PATENT DOCUMENTS

| | | |
|---|---|---|
| WO | 2017079662 A1 | 5/2017 |
| WO | 2019028458 A1 | 2/2019 |

OTHER PUBLICATIONS

Silay et al., "The All-Seeing Needle Instead of the Veress Needle in Pediatric Urologic Laparoscopy," J Endourology, 27(11)1376-1380 (Nov. 2013).

Extended European Search Report dated Mar. 2, 2021 from related application No. EP 18840663.1.

* cited by examiner

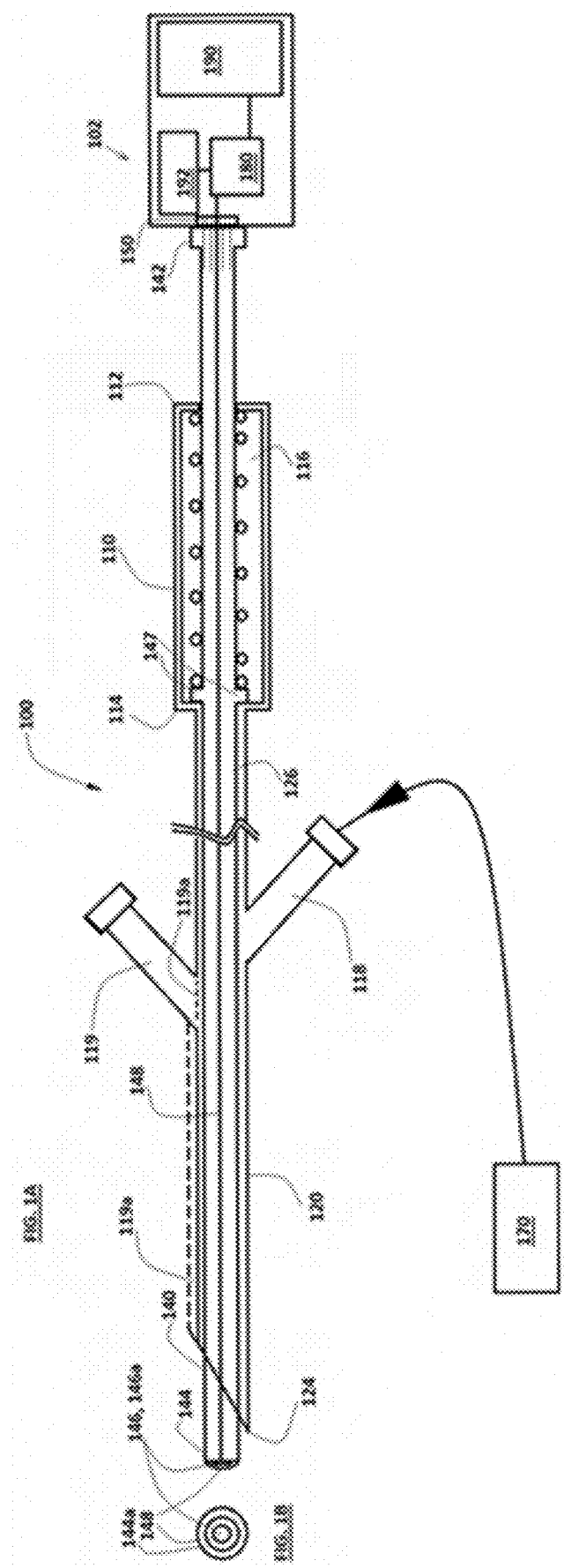

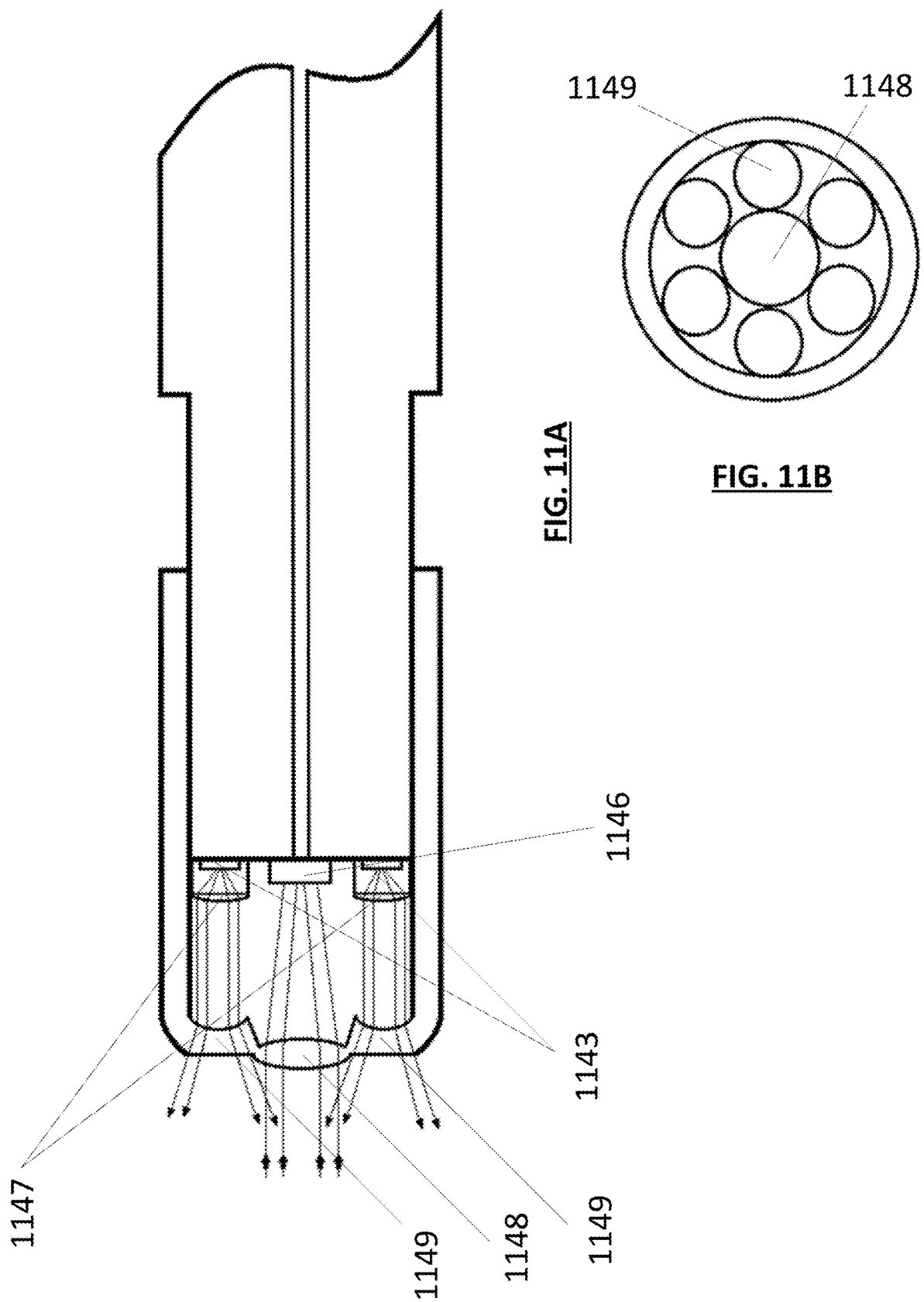

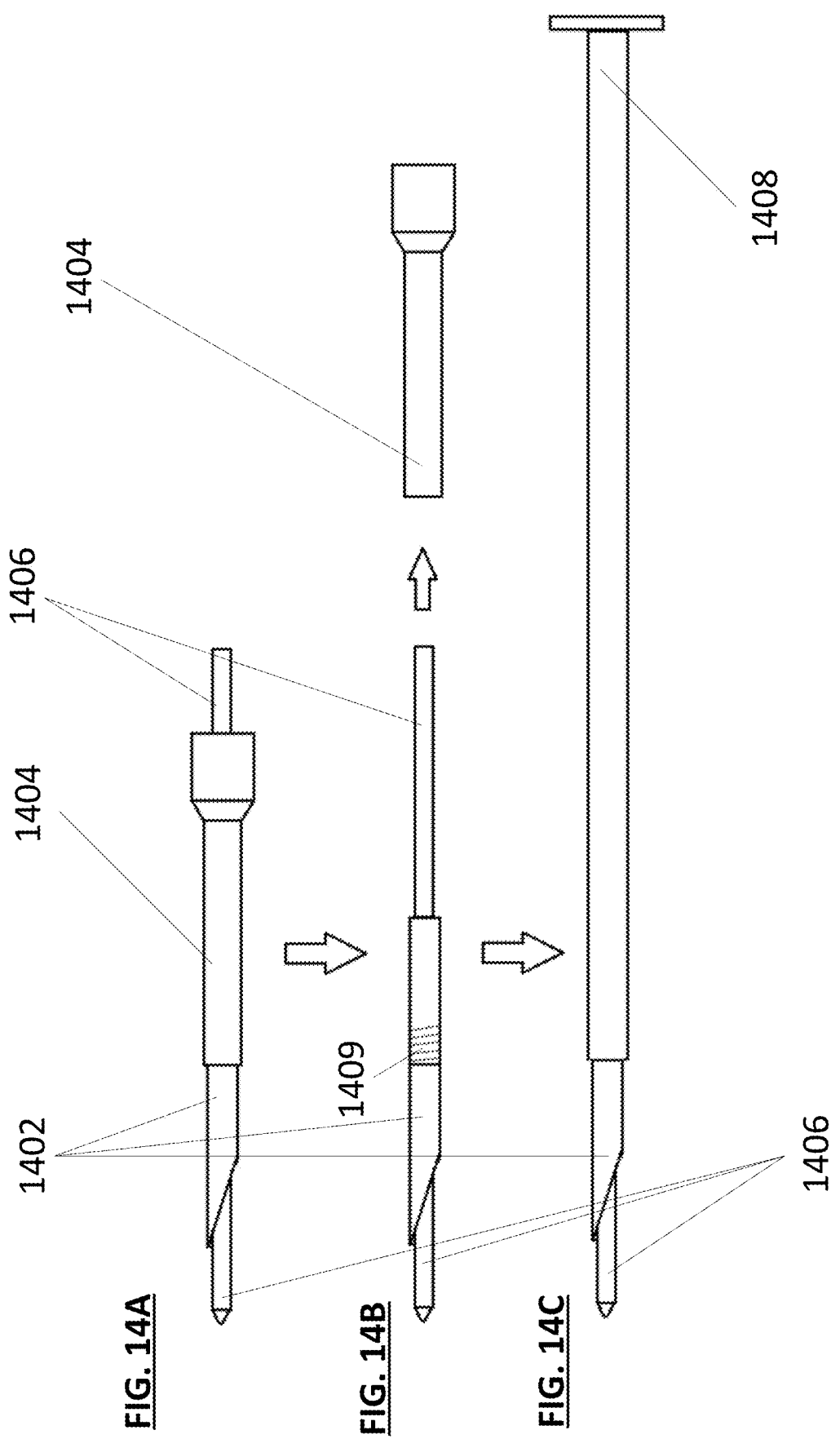

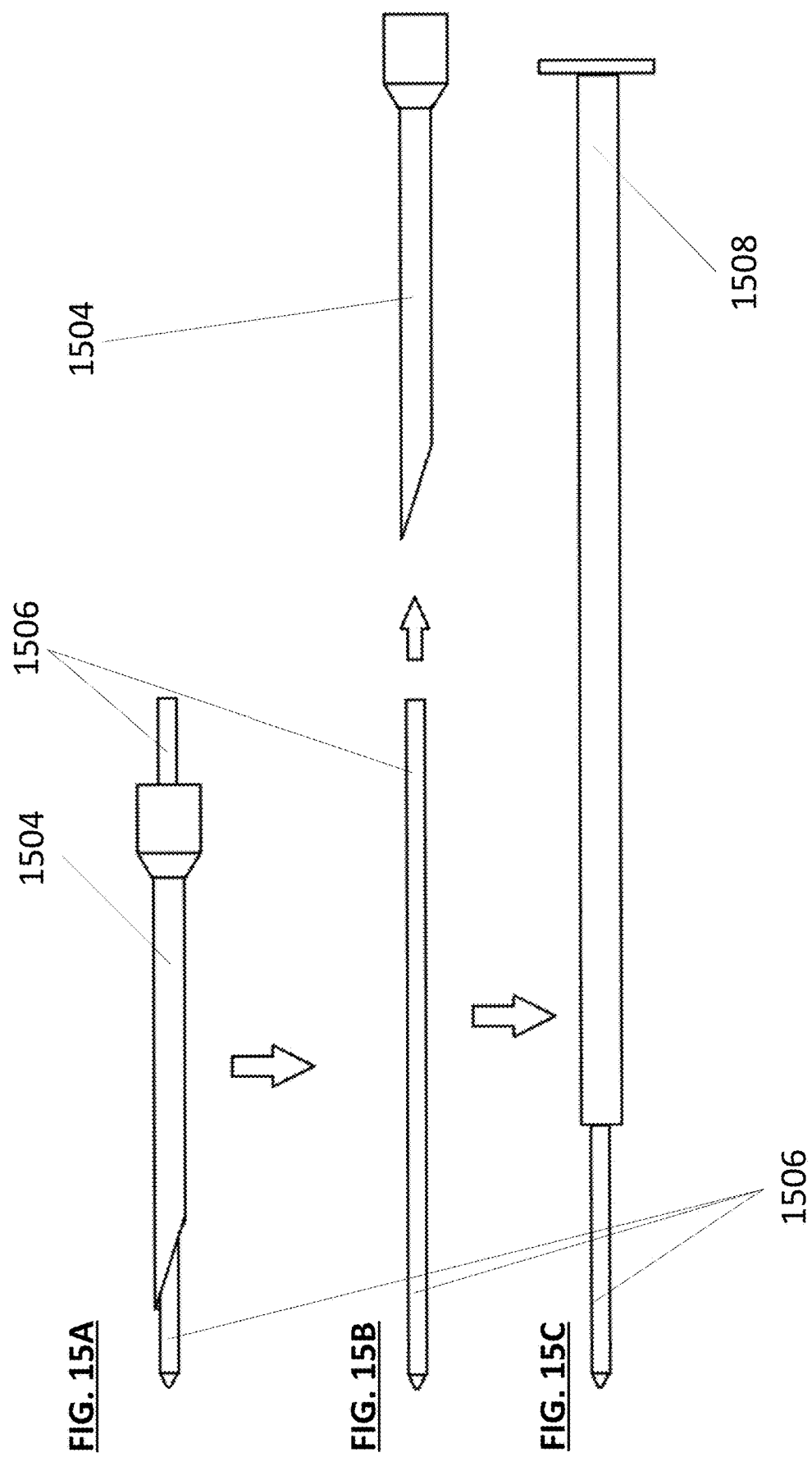

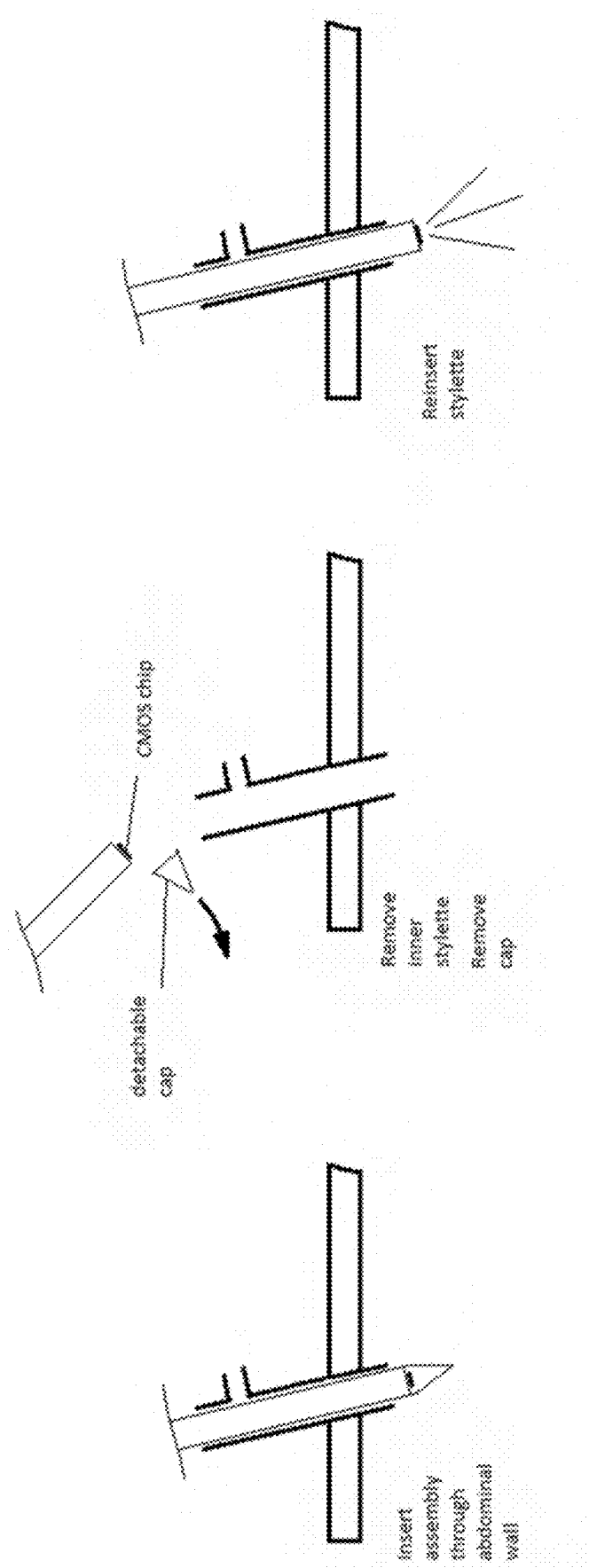

VERESS-TYPE NEEDLES WITH ILLUMINATED GUIDANCE AND SAFETY FEATURES

CROSS-REFERENCE TO RELATED APPLICATION

This patent application is a continuation-in-part of and claims the benefit of priority to International Patent Application No. PCT/US2018/45380, filed Aug. 6, 2018, which in turn is related to and claims the benefit of priority to U.S. Provisional Patent Application No. 62/541,644, filed Aug. 4, 2017. Each of the foregoing patent applications is hereby incorporated by reference in its entirety for any purpose whatsoever.

BACKGROUND

Field

This disclosure relates to instruments and methods of use therefore in the practice of laparoscopic surgery and more particularly to such devices that have utility in forming an incision and insufflating the underlying body cavity in a safer manner than prior art devices.

Description of Related Art

In the practice of minimally invasive laparoscopic surgery it is common to make a small incision through the skin and underlying tissue of the patient, or subject, adjacent the internal surgical site using a Veress needle. These needles include a tubular outer cannula with a sharpened distal end and an inner hollow cylindrical needle, or cannula, which terminates in a blunt end. A spring assembly urges the inner cannula forward so that the blunt end of the inner cannula extends beyond the cutting edge of the outer cannula. When the instrument is pressed against the skin of the patient the inner blunt cannula retracts thereby permitting the outer sharp cannula to contact the skin and advance into the tissue. As soon as a body cavity is entered, the inner blunt cannula springs forward, so that the accidental cutting of underlying organs by the sharpened outer cannula is avoided.

The Veress needle typically includes means for introducing pressurized gas, usually $CO_2$, into the proximal end of the needle so that the gas is passed on through the laparoscopic incision and inflates the body cavity to allow easy access to the surgical site. After formation of a first incision and insufflation of the body cavity, the Veress needle is typically removed and a trocar is placed through the same incision.

One problem associated with the use of such Veress needle assemblies is determining when the needle has progressed through the wall of the body cavity and its distal end has emerged within the cavity. Additionally, inadvertent injury to internal organs such as bowel and major blood vessels may occur during the insertion of a standard Veress needle. This happens because this initial entry is blind (i.e., the surgeon cannot see where the needle is going). The present disclosure provides solutions to these and other problems in the art, as set forth below.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

In accordance with one aspect, the present disclosure is directed to an apparatus that includes a handle having proximal end and distal end connected at the distal end to a hollow distally extending needle having a distal end for penetrating tissue and a proximal end, wherein the handle and hollow distally extending needle form a conduit for passing at least one of fluid or instruments therethrough. The apparatus further includes a visualization stylet having a proximal end and a distal end, said visualization stylet being slidably disposed within the conduit, wherein a distal end region of the visualization stylet includes an electronic photodetector chip mounted thereon having a distally facing surface configured to detect incoming light traveling along a proximal direction. The visualization stylet can further include a light source configured to project light beyond the electronic photodetector chip in a distal direction to provide direct illumination, wherein light originating from the light source is reflected back to the electronic photodetector chip when the apparatus is traveling through tissue. The apparatus can further include a spring housed within the handle for biasing the visualization stylet to extend past the sharp distal end of the hollow distally extending needle absent resistance by tissue against the visualization stylet.

In further implementations, the visualization stylet can include a lens element disposed on a distal tip thereof over the electronic photodetector chip. In some embodiments, the lens element can directly contact the electronic photodetector chip. In some implementations, the lens element can be axially spaced with respect to the electronic photodetector chip. If desired, the lens element can be controllably, adjustably axially spaced with respect to the electronic photodetector chip to permit a user to focus incoming light passing through the lens onto the electronic photodetector chip. For example, axial spacing of the lens element from the electronic photodetector chip along a central longitudinal axis of the apparatus can be adjusted by sliding the lens element with respect to the electronic photodetector chip.

If desired, axial spacing of the lens element from the electronic photodetector chip along a central longitudinal axis of the apparatus can be adjusted by rotating the lens element with respect to the electronic photodetector chip. In some embodiments, the lens element can include a convex lens, a plano-convex lens, or other lens. The lens element can be, for example, conically shaped, pyramid-shaped, or dome shaped, among others. In some implementations, the lens element can include a central lens configured to focus incoming light on the electronic photodetector chip surrounded by a plurality of secondary lenses configured and arranged to disperse light transmitted distally from the lens element originating from the light source.

In some embodiments, the light source can includes a bundle of fiber optic elements coupled to a source of light. If desired, the light source can include at least one micro-LED element surrounding the electronic photodetector chip. The at least one micro-LED element can include an optic disposed thereon that focuses and directs light from the at least one micro-LED element onto at least one of the secondary lenses. If desired, the lens element can include a central lens configured to focus incoming light on the electronic photodetector chip surrounded by an annular region of the lens, wherein the central lens is radially separated from the annular region of the lens by at least one fluid flow channel configured and arranged to direct a jet of cleaning fluid over at least a portion of the central lens. In some implementations, the central lens and the annular region of the lens can be integrally molded. If desired, the central lens and the annular region of the lens can be formed from at least two discrete components.

In some implementations, the apparatus can further include at least one fluid flow channel configured and arranged to direct a jet of cleaning fluid over at least a portion of a central lens disposed at the distal end of the visualization stylet. The at least one fluid flow channel can be defined by at least one tubular member slidably disposed along the visualization stylet, the tubular member(s) defining a plurality of spray openings in a side wall thereof. If desired, the tubular member(s) can be formed from a shape memory material. A distal region of the tubular member(s) can be advanced distally out from the visualization stylet, and takes on a heat set curvature that causes the tubular member to bend toward the lens element.

In some embodiments, if correspondingly equipped, the axial spacing of the lens element from the electronic photodetector chip can be adjusted by actuating an actuator near a proximal end of the visualization stylet. If desired, any of the lens elements disclosed herein can include at least one vent hole therein, for example, for passage of insufflation gas, and/or to facilitate the focusing of the lens element by permitting axial repositioning of the lens with respect to the rest of the visualization stylet.

In some embodiments, the at least one fluid flow channel can be defined by at least one tubular member attached to an inner wall of the conduit of the hollow needle. The tubular member can define a plurality of spray openings in a side wall thereof configured and arranged to clean the lens by directing a transverse flow of fluid across the lens. The visualization stylet can also define at least one elongate insufflation conduit therein configured to pass insufflation gas therethrough to a distal end region of the apparatus. Insufflation gas can exit through at least one opening defined through a sidewall of the visualization stylet near a distal tip of the visualization stylet. The visualization stylet can be formed at least in part from a light transmitting material. The light source can include at least one LED disposed in the proximal end of the handle, for example.

In some implementations, the apparatus can further include a gas introduction port for receiving insufflation gas from a gas source. The visualization stylet can be configured to be withdrawn proximally to establish a flow path for insufflation gas to pass through the apparatus. The visualization stylet can further include a conductor for directing signals received from the electronic photodetector chip to a processor. The processor can be attached to the visualization stylet. If desired, the apparatus can further include a display screen for displaying images captured by the electronic photodetector chip. If desired, the apparatus can further include a battery for powering the electronic photodetector chip, processor and display screen.

The disclosure further provides a variety of methods for treating subject, such as a patient. For example, a first embodiment of a method is provided of using devices such as those described herein. Some of the methods can include creating a small superficial incision in skin of an abdomen of a subject, advancing a distal end of a hollow distally extending needle including a visualization stylet disposed therein through successive layers of an abdominal wall of the subject while viewing tissue being advanced through by way of the visualization stylet in real time, the visualization stylet being configured to view in a distal direction, and stopping advancing the distal end of the hollow distally extending needle upon observing the visualization stylet extending distally with respect to the hollow distally extending needle indicating that an abdominal cavity of the subject has been reached.

In some implementations, the method can further include commencing insufflation through the hollow distally extending needle after stopping advancing the distal end of the hollow distally extending needle. Commencing insufflation through the hollow distally extending needle can further include removing the visualization stylet through the proximal end of the hollow distally extending needle and injecting gas through the hollow distally extending needle. If desired, the method can further include comprising directing signals from the electronic photodetector chip to a processor. The method can further include directing signals from the processor to a display screen.

In some embodiments of the method, the hollow distally extending needle can act as a sheath that at least partially covers the visualization stylet along its length. The handle can include a cannula that is removably attached to the hollow distally extending needle. The method can further include, after insufflation, removing the cannula from the hollow distally extending needle and withdrawing the cannula proximally over the visualization stylet. Removing the cannula can include disconnecting a threaded connection joining the hollow distally extending needle and the cannula. If desired, the method can further include attaching a proximal extension to at least one of the hollow distally extending needle and the visualization stylet to form an assembly, and performing a laparoscopic procedure using the assembly as an endoscope. If desired, the method can further include separating the hollow distally extending needle and handle from the visualization stylet and removing one of the visualization stylet and hollow distally extending needle and handle from the subject. Once the visualization stylet is removed, the method can include leaving the hollow distally extending needle in place to function as a cannula for performing a further procedure.

The method, can further include, in some embodiments, removing a lens cap from the visualization stylet, and reintroducing the visualization stylet into the handle and the hollow distally extending needle without the lens cap. The lens cap can be removed, for example, by articulating the lens cap away from the distal end of the visualization stylet on a hinge.

Disclosed methods can also include, for example, directing a cleaning fluid including at least one of a liquid or gas at least partly in a transverse direction across the distal end of the visualization stylet while inside the subject to enhance visualization. Directing a cleaning fluid can include distally extending a cleaning wand that is configured and adapted to direct cleaning fluid toward the distal end of the visualization stylet. Directing the cleaning fluid can include directing the cleaning fluid through the visualization stylet and out through at least one opening at the distal end region of the visualization stylet. Directing the cleaning fluid can include directing the cleaning fluid through a lens located at the distal end of the visualization stylet. The cleaning fluid can be directed at least partially along a radially inward path across a central region of the lens. Directing the cleaning fluid can include directing the cleaning fluid through the hollow distally extending needle. If desired, directing the cleaning fluid can include directing the cleaning fluid through at least one tubular passage disposed between the visualization stylet and an inner bore of the hollow distally extending needle, wherein the at least one tubular passage is attached to the inner bore of the hollow distally extending needle.

In further accordance with the disclosure, the method can include removing the hollow distally extending needle and handle, leaving the visualization stylet in place. If desired, the method can further include adding a proximal extension to the visualization stylet to form an assembly, and using the assembly as an endoscope. The method can further include disposing a cannula having a bore diameter at least twice the diameter of the visualization stylet over the visualization stylet, causing the tissue to dilate radially outwardly. If desired, the visualization stylet can have a diameter of 1 to 2 mm, for example, and the cannula can have a 5 mm bore. If desired, the visualization stylet can have a diameter of 1 to 2 mm, and the cannula can have a 10 mm bore.

If desired, the method can further include withdrawing the visualization stylet, leaving the cannula in place. The method can further include introducing a further instrument through the cannula. The further instrument can be an endoscope configured to match a size of a bore of the cannula.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the disclosed methods and systems. Together with the description, the drawings serve to explain principles of the disclosure.

BRIEF DESCRIPTION OF THE DRAWINGS

Other objects, advantages and applications of the present disclosure will be made apparent by the following detailed description. The description makes reference to the accompany drawings in which:

FIGS. 1A-FIG. 1B present various views of a first embodiment in accordance with the present disclosure.

FIGS. 11A-FIG. 11B present various views of a further embodiment of visualization stylet distal tip and lens configuration in accordance with the present disclosure.

FIGS. 14A-FIG. 14C present views of steps of a method in accordance with the present disclosure.

FIGS. 15A-FIG. 15C present views of steps of still a further method in accordance with the present disclosure.

FIGS. 16A-FIG. 16C present views of steps of yet another method in accordance with the present disclosure.

DETAILED DESCRIPTION OF PREFERRED EMBODIMENTS

Figure 2A:
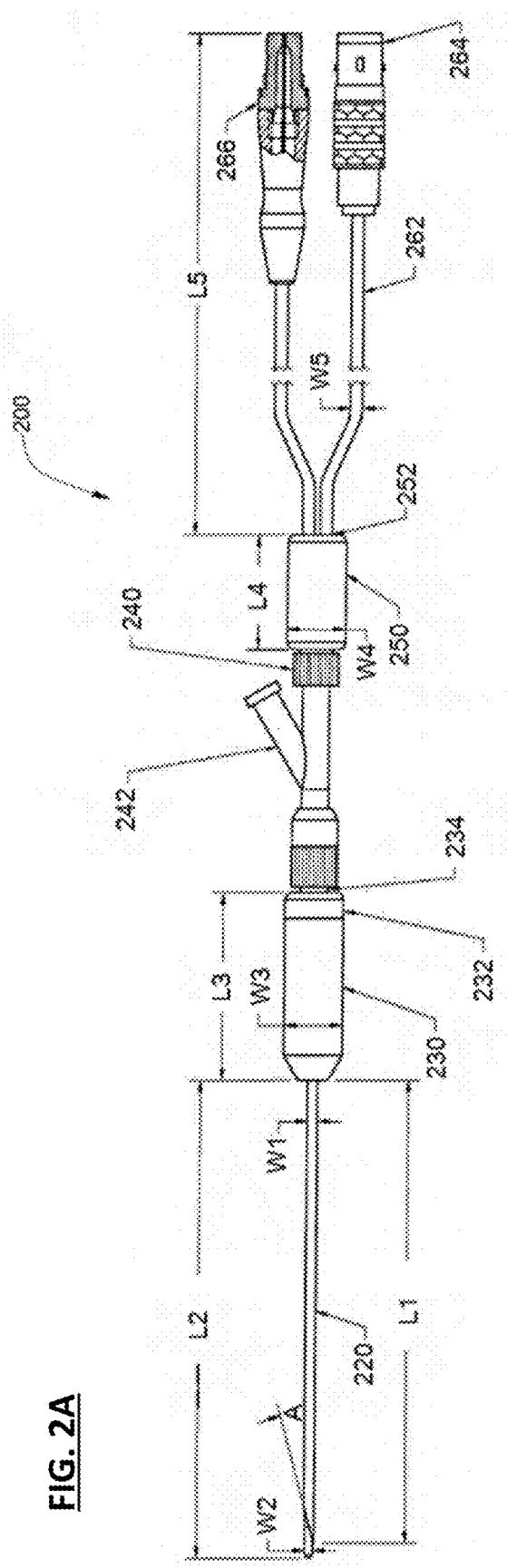
FIGS. 2A-FIG. 2C present various views of a second embodiment in accordance with the present disclosure.

A preferred embodiment of the disclosure, illustrated in FIGS. 1A-1B, acts as a Veress needle to form an incision into a body cavity, as an insufflator to inject gas into the cavity, and as a visualization tool to monitor progress of the Veress needle as it traverses through tissue while progressing toward the abdominal cavity.

For purposes of illustration, and not limitation, as embodied herein and as illustrated in FIG. 1, an apparatus 100 is provided in the form a Veress-type needle. The apparatus 100 includes a handle 110 having proximal end 112 a distal end 114 and a hollow elongate passage 116 therethrough that is in turn connected to a hollow distally extending needle 120 having a sharp distal end 124 for penetrating tissue and that defines a hollow elongate passage 126 therethrough. The passages 116, 126 of the handle 110 and the needle 120 cooperate to form a conduit for passing at least one of fluid or instruments therethrough.

The apparatus 100 further includes a visualization stylet 140 that in turn includes a proximal end 142 and a blunt distal end 144. The visualization stylet 140 is slidably disposed within the conduit (116, 126) of the handle 110 and needle 120. As illustrated, a distal end region of the visualization stylet 140 includes an electronic photodetector chip 146 mounted thereon (or therein) having a distally facing surface 146a including an array of photo sensors that are configured to detect incoming light traveling along a proximal direction (i.e., toward the distal end of the apparatus 100). The apparatus 100 further includes a light source 150, such as a LED disposed in the handle 110, configured to project light beyond the electronic photodetector chip 146 in a distal direction to provide direct illumination of an area being traversed by the apparatus 100. In operation, light originating from the light source 150 traverses the body of the visualization stylet (which can be made from light transmissive plastic, for example) and illuminates the tissue immediately distal to the visualization stylet 140. That light is reflected back to the electronic photodetector chip 146. In accordance with further implementations, one or more fiber optic light transmitting fibers can be used to transmit light from a light source either inside or outside the handle 110 through the device to the distal end of the device. Light may be transmitted using fiber optic fibers down the visualization stylet, and/or the needle 120 and handle 110.

The apparatus 100 still further includes a spring 160 housed within the handle 100 for biasing the visualization stylet 140 (via boss(es)) 147 to extend past the sharp distal end 124 of the needle 120 absent resistance by tissue against the visualization stylet. Thus, in use, while the apparatus is urged against tissue, the visualization stylet urges against the tissue with the needle distal end 124. Once the apparatus traverses the abdominal wall, however, and enters the abdominal cavity, visualization stylet 140 is urged forward by spring 160 beyond the needle distal end 124, thereby preventing the needle 120 from cutting through any additional tissue in the abdominal cavity, including, for example, bowels, blood vessels, and the like.

If desired, the visualization stylet 140 can include a lens element 148 disposed on a distal tip thereof over the electronic photodetector chip 146. Preferably, the lens element can include a solid or hollow piece of plastic, glass, or other suitable material that can be attached to the electronic photodetector chip. In some implementations, the electronic photodetector chip 146 can be integrally molded into a clear plastic body of the visualization stylet 140, wherein a lens is molded over the electronic photodetector chip and further wherein a conductor 148 leading away from the electronic photodetector chip can be directed, for example, along a central axis of the visualization stylet (or the device overall) either embedded in the material of the visualization stylet (via an overmold), or by directing it through a hollow passage (not shown) along the central axis of the visualization stylet 140. If desired, the molding process can result in clear plastic material directly contacting the surface of the electronic photodetector chip.

The visualization stylet can thus be formed from a light transmissive (e.g., transparent or translucent) material such as PET or acrylic, or can be made from other material with one or more fiber optics traversing the length of the visualization stylet to transmit light from the light source. As illustrated, an annular outer area 144a of the distal end 144 of the visualization stylet 140 proximal to the electronic photodetector chip 146 can be provided wherein the electronic photodetector chip is in the middle of the distal end 144 to permit light to be conducted down the visualization stylet, past the electronic photodetector chip 146, and through the lens 148.

As further illustrated, the handle 110 can be provided with a gas introduction port 118 for receiving insufflation gas from a gas source 170. Also, if desired, a flush port 119 can be provided that can direct a liquid in the annular space defined between the handle 110/needle 120 and the visualization stylet 140 to clean the distal end of the visualization stylet. Additionally or alternatively, a flush port can be provided as a parallel lumen structure, indicated by 119a. In some implementations, the visualization stylet 140 is configured to be withdrawn proximally along passages 126, 116 to establish a flow path for the insufflation gas. For example, the visualization stylet need only be withdrawn proximal to the gas introduction port to provide a clear path for directing insufflation gas into the abdominal cavity of a subject.

As mentioned above, the conductor 148 can be provided for directing signals received from the electronic photodetector chip to a second location, such as a processor 180. The processor can thus be coupled to the visualization stylet. The processor can then, in turn, be connected to a display screen 190 for displaying images captured by the electronic photodetector chip 146. The display device 190 can be a large LCD screen that is a part of a separate computer system, or it may be provided as a small local screen attached to the processor and a battery 192 in a module attached to a proximal end 102 of the apparatus, for example. If desired, an adapter (not shown) can be provided to connect the apparatus 100 to a laparoscopic camera, light source and monitor that is available in the operating room.

The disclosure further provides a method of using an apparatus as described herein to more safely accomplish an insufflation procedure in preparation for a laparoscopic surgical procedure in the abdomen. The method includes puncturing a surface of skin of a subject with a sharp distal end of a hollow needle (e.g., 124) of the apparatus (e.g., 100). The method further includes advancing the distal end of the hollow needle (e.g., 124) through successive layers of the abdominal wall of the subject while viewing the tissue being advanced through via the visualization stylet in real time. The process still further includes stopping advancement of the distal end of the hollow needle when reaching the abdominal cavity. A user can note that the abdominal cavity has been reached when the visualization stylet shoots distally under force of the spring 160 past the distal end 124 of the needle 120. At this point, the visualization stylet 140 can be retracted proximally, such as under manual action, and the method can further include commencing insufflation through the hollow needle.

Figure 2B:
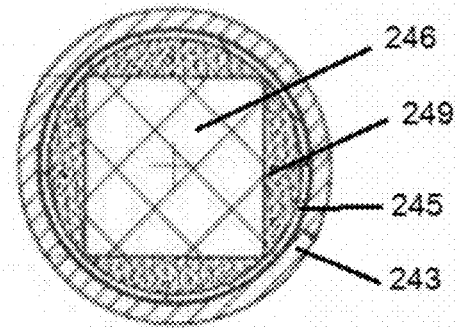
Figure 2C:
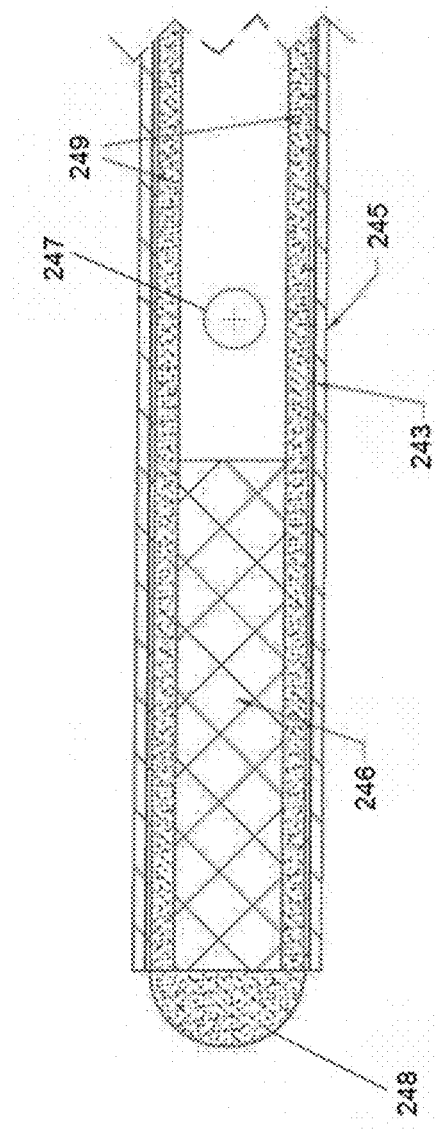

In further accordance with the disclosure, a second embodiment of a visualization insufflation needle assembly 200 is presented in FIGS. 2A-2C. With reference to FIG. 2A, the assembly includes an outer sheath 220 with an angled, sharpened distal tip for penetrating tissue, including a spring loaded visualization stylet, similar to that in FIGS. 1A-1B. The outer sheath can be made, for example, from stainless steel tubing, and have a length L1 between for example, about 2 and about 6 inches, in increments of about one eighth of an inch. Visualization stylet can have a similar length L2. The diameter, or width, W2, of the visualization stylet can be, for example, between about 0.050 to about 0.1 inches in increments of 0.01 inches. The sheath can have a diameter or width W1 between about 0.06 and 0.12 inches, in increments of 0.01 inches. The distal tube 220 is attached at a proximal end to a cannula body 230 with a cannula cap 232 that may be removable. A spring biasing mechanism similar in functionality to that illustrated in FIG. 1A is contained within cannula body 230 that is operably attached to the visualization stylet for biasing it beyond the tip of the outer tube 220. Cannula 230 can have a length L3 between, for example, about 1.5 and 2.0 inches, in increments of one sixteenth of an inch, and a width or diameter W3 between about 0.4 and 0.8 inches, in increments of about 0.05 inches. The proximal end of cap 232 is adjacent to a female Luer lock connector 234 with a Y connector 242 and proximal male Luer lock connector 240. Connector 240 is received by an electronics connector 250 having a proximal plug 252 that in turn connects to a light source 266 for directing light down the visualization stylet to provide illumination and to a camera output connector 264 for directing digital image data to a processor and/or screen. If desired, connector 264 can include specialized circuitry specifically configured for converting data received from the photodetector in the visualization stylet into a video output signal. Sheathing 262 is provided for protecting the video output cable. Body 250 can have any suitable length L, for example, between about 0.75 and 2.0 inches in increments of 0.1 inches and a diameter or width W4 between about 0.4 and 0.8 inches, in increments of about 0.05 inches. Length L5 can be between, for example, 8 and 24 inches or in any increment therebetween of about one quarter inch.

FIGS. 2B and 2C present end and cross sectional views of the distal end region of the visualization stylet. FIG. 2B shows a view of the distal end with the lens 248 removed, thereby illustrating the photodetector array 246 and surrounding structures. Light is transmitted distally through illumination bundle 249 which surrounds the photodetector array 246. Illumination bundle is in turn surrounded by a polymeric illumination sheath 243, made for example of a suitable polymer such as polyimide. A transverse opening 247 is provided for permitting insufflation gas passing down the hollow bore of the visualization stylet to pass through the outer wall of the visualization stylet for insufflation of the peritoneum. Conductors (not shown) are connected to array 246 to conduct data indicative of light received by the array proximally and out of device 200. Sheath 243 is in turn surrounded by a (preferably metallic) tubular member 245 that is attached at its proximal end to a spring that is also attached to cannula body 250.

The visualization stylet, particularly the distal end region of the visualization stylet, can be made in a variety of ways and having a variety of features. FIGS. 3-11A illustrate cross sectional views of different embodiments of this portion of the device (e.g., 100, 200) that include like reference numbers for similar structures.

Figure 3:
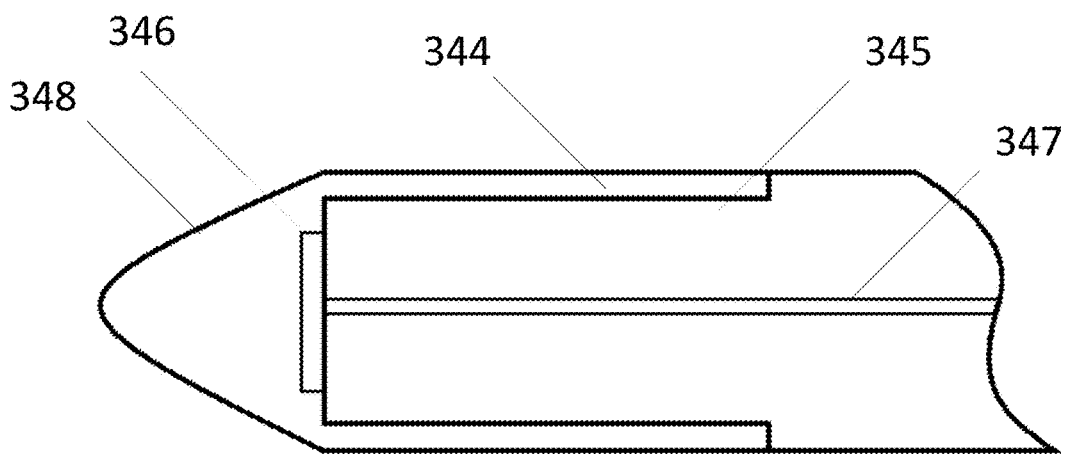
FIGS. 3-10 present various embodiments of visualization stylet distal tip and lens configurations in accordance with the present disclosure.
Figure 4:
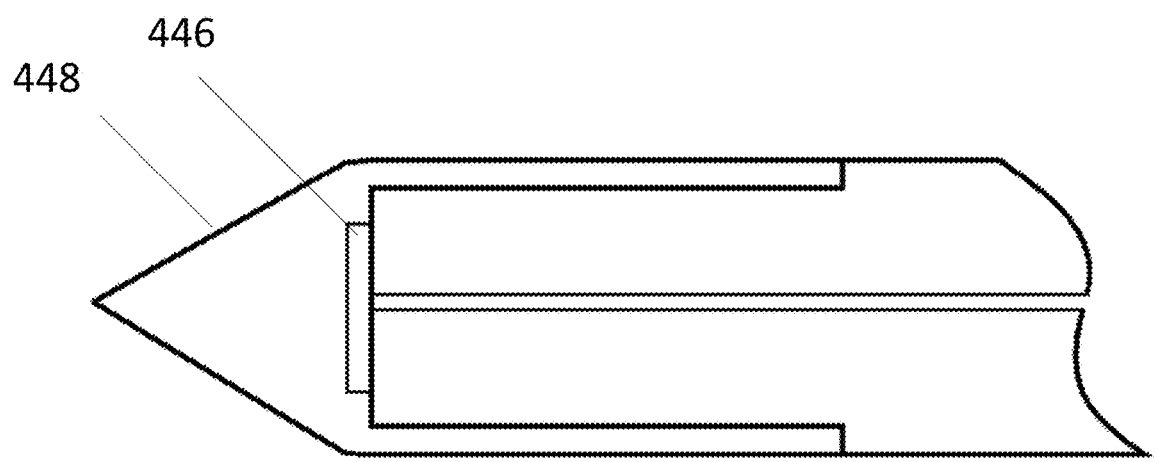

FIG. 3 illustrates such a distal region having a distal lens cap 348 that is substantially conically shaped with a curved tip that can be useful for blunt dissection. The cap is defined by a solid or hollow end region that can be a conic section, for example, that transitions into an annular tubular region that is slidably received, for example (and adhered or otherwise attached to) a recessed portion 345 of a main body portion of the visualization stylet, which in turn includes a photodetector array 346 (shown in simplified form). Illumination bundles and other structures similar to the embodiment of FIGS. 2B-2C can also be provided. One or more central passages 347 can also be provided to accommodate the passage of data conductors or the passage of liquid or gaseous flushing fluids for irrigating the tip of lens 348, as desired. FIG. 4 illustrates a distal end region that alternatively includes a sharp conical, or pyramid (e.g., 3, 4, 5, or 6 sided) shaped lens 448.

Figure 5:
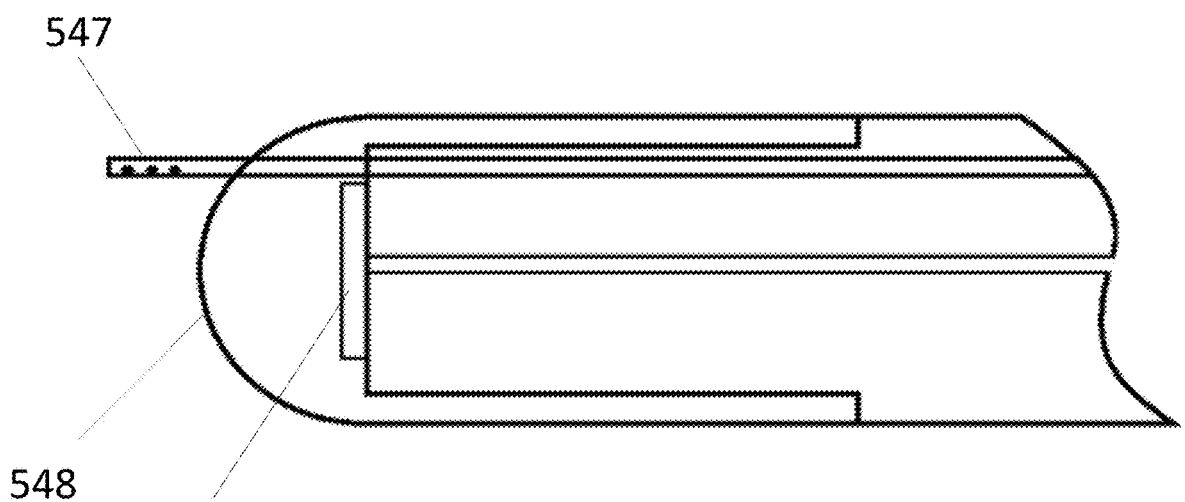

FIG. 5 is similar to the embodiments of FIGS. 3 and 4, but includes a dome shaped lens 548, and photodetector 546 and the like. Additionally, the embodiment of FIG. 5 includes a first embodiment of a lens flushing mechanism that includes a tubular body 547 directed through the body of the visualization stylet that includes a plurality of flushing holes. The body 547 can be formed from a hypotube, for example, with a sealed distal tip and one or more transversely formed holes through the hypotube to direct a fluid jet across the lens, wherein the fluid can include, for example, saline, another liquid and/or a gaseous substance, such as carbon dioxide insufflation gas. Tube 547 is preferably slidably movable with respect to visualization stylet, and can be controllably deployed by advancing it distally with respect to the visualization stylet distal tip. In one embodiment, the tube 547 is made from a shape memory material (e.g., Ni Ti alloy) wherein it is heat set to bend around the tip to direct cleaning liquid and/or gas at the tip along a direction that is partially transverse and partially axial in a proximal direction. The tube 547 can still be retracted proximally into a straight guide channel. If desired, more than one such tube 547 (Ni Ti or other material) can be provided at various locations to effectuate efficient cleaning. In further embodiments of devices and methods (not illustrated), a mechanical wiping seal or wiping pad is provided inside the cannula or sheath for wiping off the distal tip of the visualization stylet.

Figure 6:
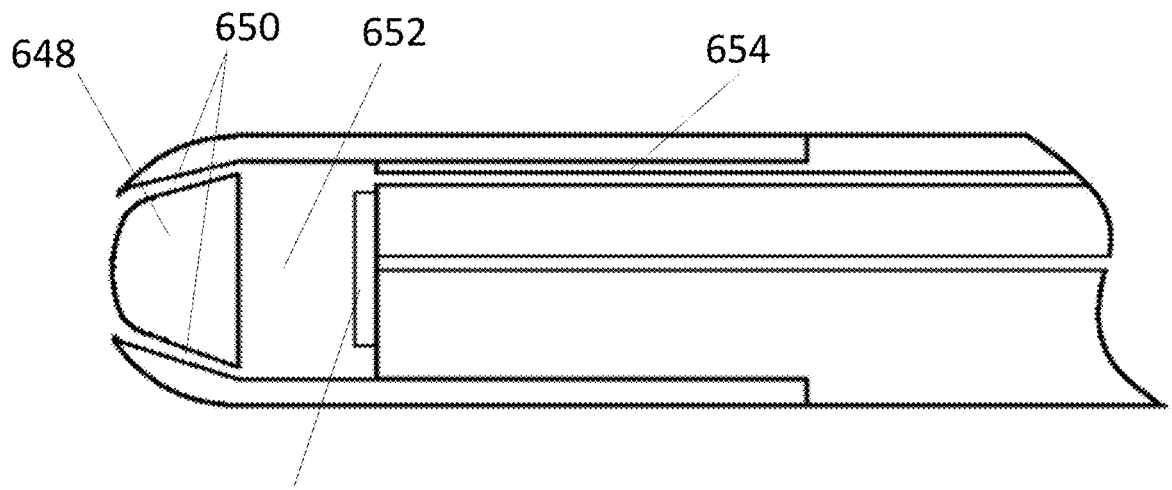

FIG. 6 illustrates an embodiment similar to that of FIG. 5, wherein that a cavity 652 is provided between the distal tip of the photodetector array and the distal lens 648. If desired, a flush channel 654 can be provided for directing liquid and/or gas into cavity 652 for enhancing optical performance. In such an instance, a small vent hole can be provided. Moreover, if desired, one or more circumferentially located flush channels 650 can be provided that pass through the lens 648. If desired, in some embodiments, such flush channels can be distributed across the surface of the tip to help keep it clean. Preferably the index of refraction of the flushing fluid, e.g., a liquid, is matched to that of the material of the tip to minimize image distortion. Furthermore, if desired, the tip of the central region of the lens can be located proximally with respect to the circumference of the lens. This permits, as shown, flush passages that vector flushing fluid (liquid and/or gas) over the face of the central portion of the lens 648. Moreover, it will be appreciated that the flush passages do not necessarily need to be directed radially inward, or at least not significantly, in order to obtain a cleaning benefit. Specifically, Applicant believes that suitably configured cleaning passages and suitable flow rates for liquids (e.g., saline) and/or gases (e.g., carbon dioxide) will result in cleaning fluid streams that hug the surface of the lens, even as it curves toward the distal tip. This is known in fluid mechanics as the "Coandă effect". Specifically, the Coandă effect is the phenomena in which a jet flow attaches itself to a nearby surface and remains attached even when the surface curves away from the initial jet direction. Thus, it is possible to have the benefits of cleaning passages while minimizing their effect on reduction of field of view of the lens, and/or image distortion through the lens. Thus, for example, a liquid stream can be ejected through the cleaning passages and followed by a burst of gas flow. Alternatively, simply a gas flow can be used through the passages.

If desired, the distal tip can be formed by fitting a separate lens 650 into the circumferential region. This can be done, for example, by attaching the lens center 650 to the photodetector 646 or to the light transmitting bundles surrounding it, by extending the proximal face of the lens central region so that it abuts the photodetector and/or surrounding area. In that instance, the annular outer portion of the lens can be provided in the form of a separate tubular member that slips over the center region of the lens. If desired, in that instance, the lens center 650 and/or the peripheral region can be provided with standoffs, preferably that are circumferentially disposed (preferably three, but other amounts can be used), to separate and align the inner central portion of the lens 650 with the annular outer portion, and also to define the flow path for the flush channels.

Figure 7:
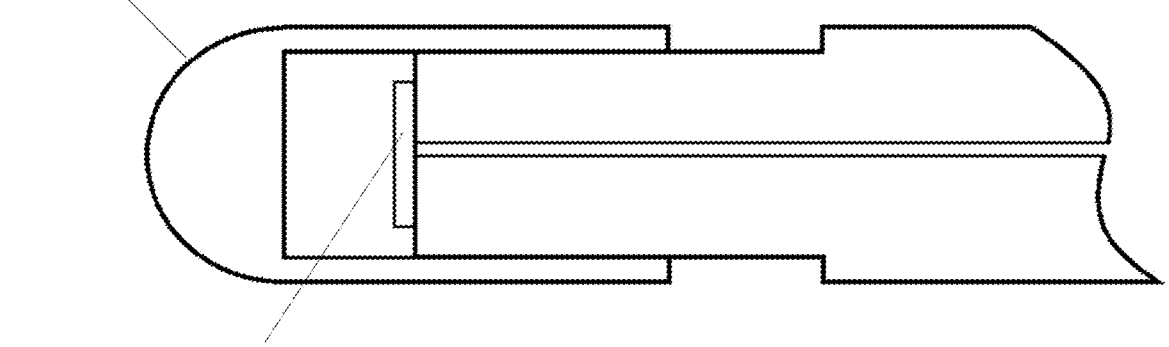
Figure 8:
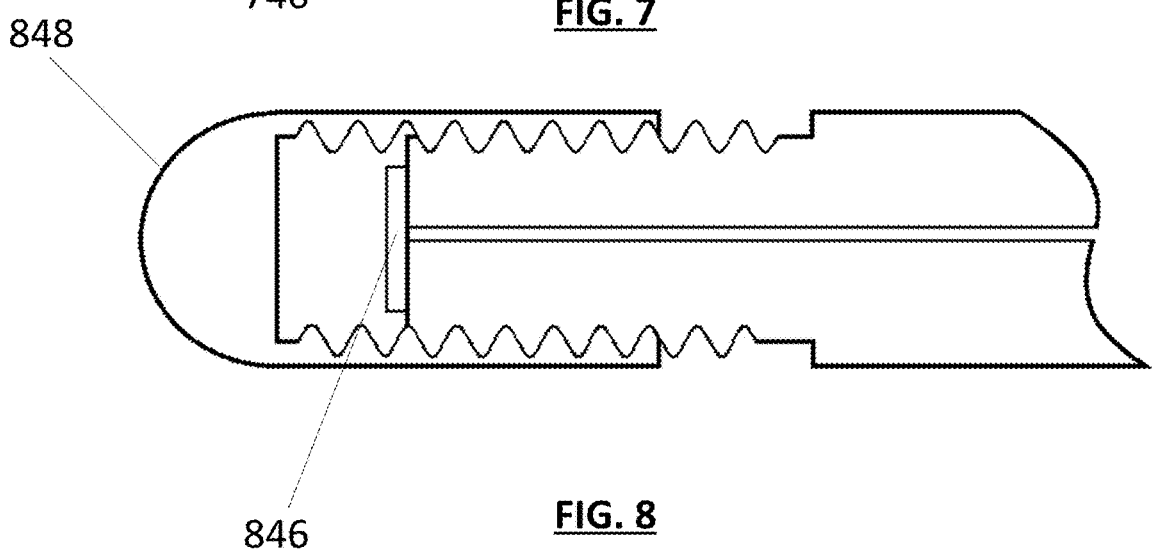
Figure 9:
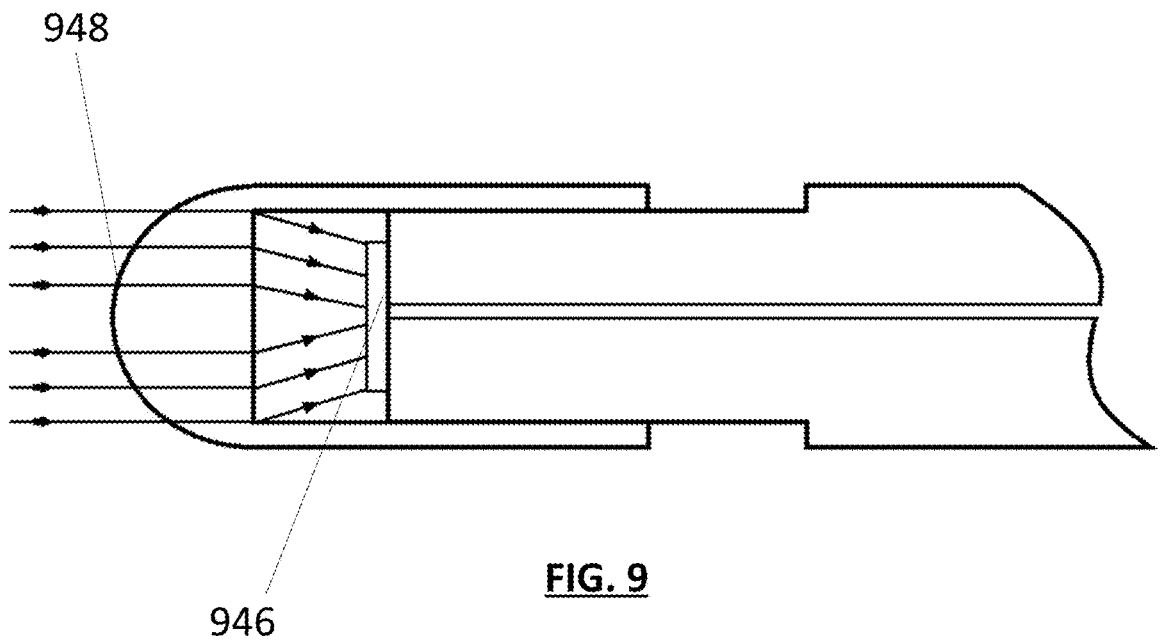
Figure 10:
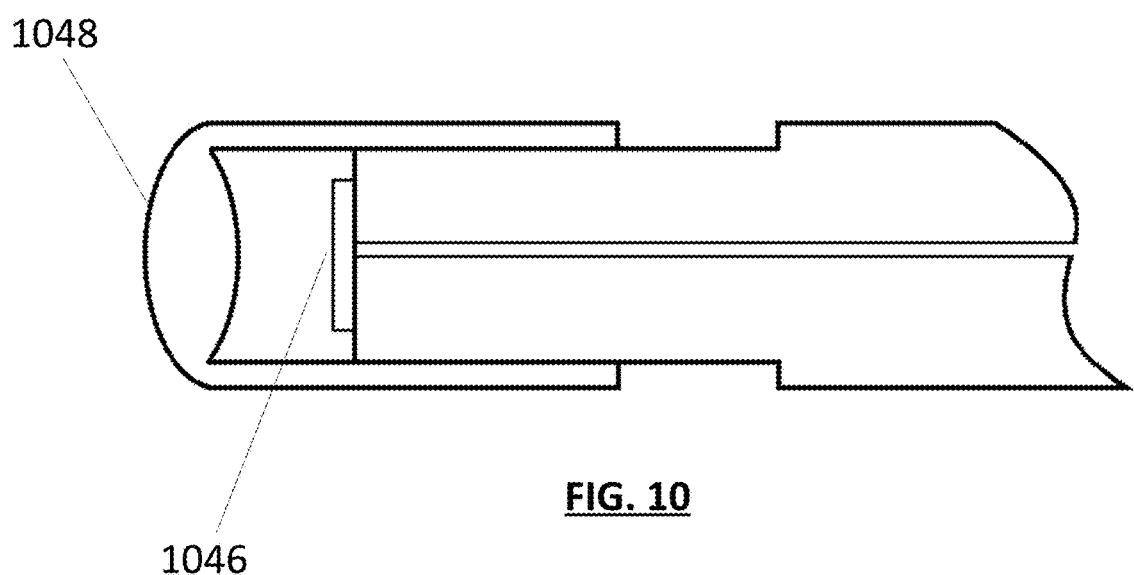

FIG. 7 illustrates a further embodiment wherein the lens 748 is slidably mounted on the visualization stylet to permit adjusting the axial distance between the lens and the photodetector 748 to accommodate for focal length of the lens. This can be accomplished by an interference fit that is adjustable, or by way of a push pull actuation arrangement discussed below with respect to FIGS. 12A-12B. FIG. 8 shows an alternative focal length adjustment arrangement that utilizes a screw thread connection between the lens 848 and the body of the visualization stylet to adjust the axial distance between the lens and photodetector 846. FIG. 9 illustrates a ray diagram showing the lens 948 in the form of a plano-convex lens that is configured to focus incoming light radially inwardly on the photodetector 946. FIG. 10 illustrates a similar arrangement for a convex lens. The curvature of the lens (or lack thereof) can be selected to accommodate narrower or broader fields of view.

FIGS. 11A and 11B illustrate a more complex lens arrangement wherein light being delivered for purposes of illumination goes through one or more separate lenses from the lens used to collect incoming light onto the photodetector 1146. Specifically, the lens can be a molded lens assembly having, for example, a central portion 1148 that is a convex lens (or other lens) for collecting light and focusing it on the photodetector 1146, and one or more (e.g., 2, 3, 4, 5, 6) circumferentially arranged smaller lenses 1149 for distributing light from the light bundle outwardly. Preferably, the optics are arranged to minimize internal reflections in the lens and reduce the mixing of outgoing and incoming light. If desired, the light source can include micro-LEDs 1143 that are mounted underneath a suitable optic, or lens, 1147, having optics matched to deliver light out of secondary lenses 1149. If desired, the electronic photodetector chip and micro-LEDs can be formed on the same chip or circuit board and have optics molded thereover to simplify manufacture.

Figure 12A:
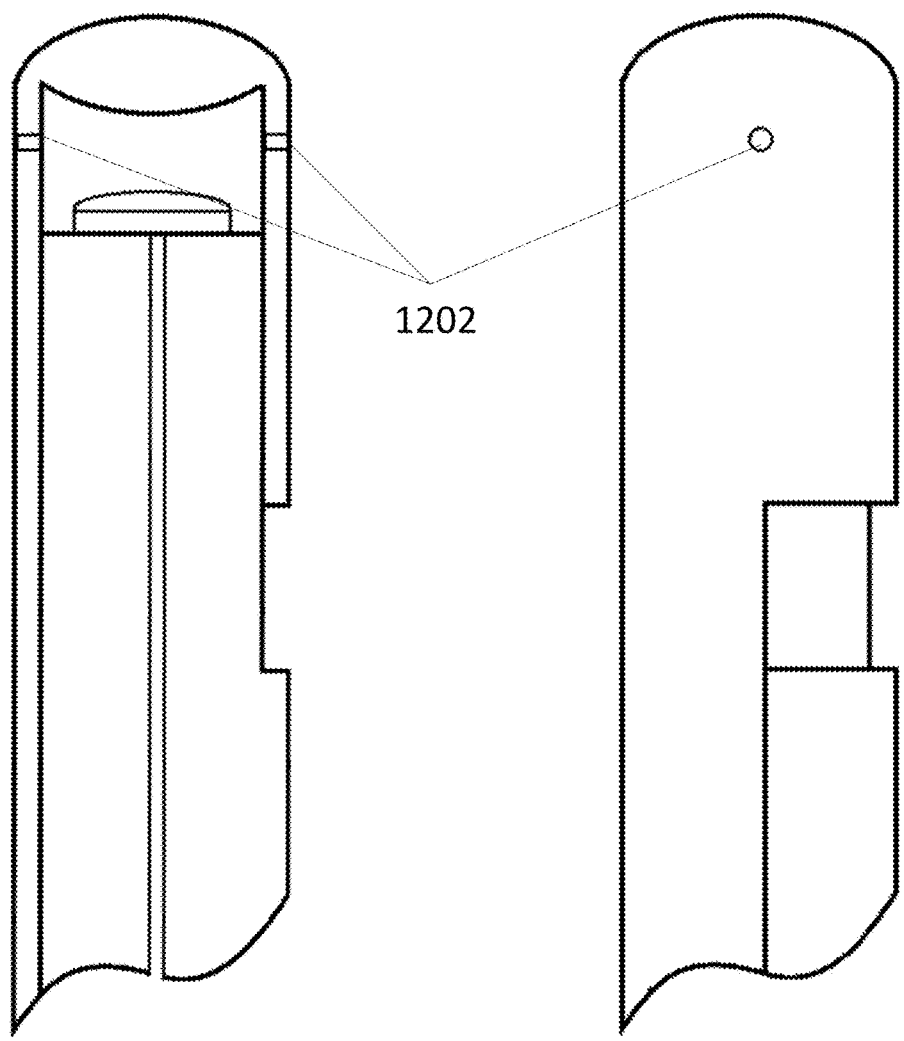
FIGS. 12A-FIG. 12B present a cross sectional and side view, respectively of a further embodiment of visualization stylet distal tip and lens configuration in accordance with the present disclosure.
Figure 12B:
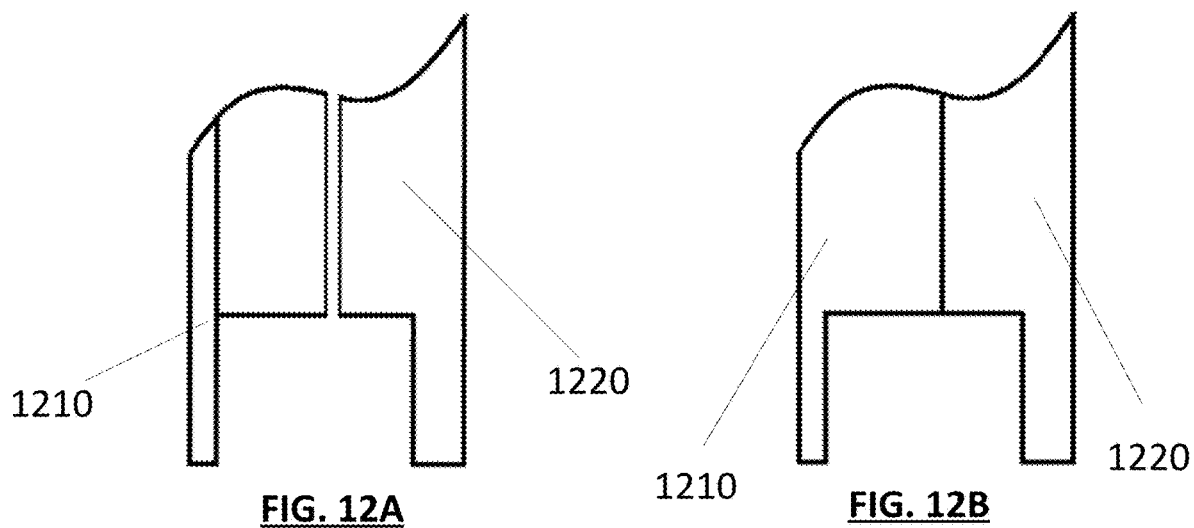

FIGS. 12A-12B illustrate an embodiment of an visualization stylet that has a push-pull actuator for adjusting the axial distance between the lens and the photodetector. For example, a first portion of the actuator 1210 is connected to the distal lens, and a second portion 1220 is attached to the central portion of the visualization stylet. The axial length can be accomplished, for example, by a simple push pull arrangement. Or, if more precision is required, an actuator using a screw thread can be used for a finer adjustment. Vent holds 1202 can be provided to permit liquid or other fluid to flow into or out of the cavity space between the lens and the photodetector. It will be appreciated that such vent holes can be provided in any embodiment herein.

Figure 13A:
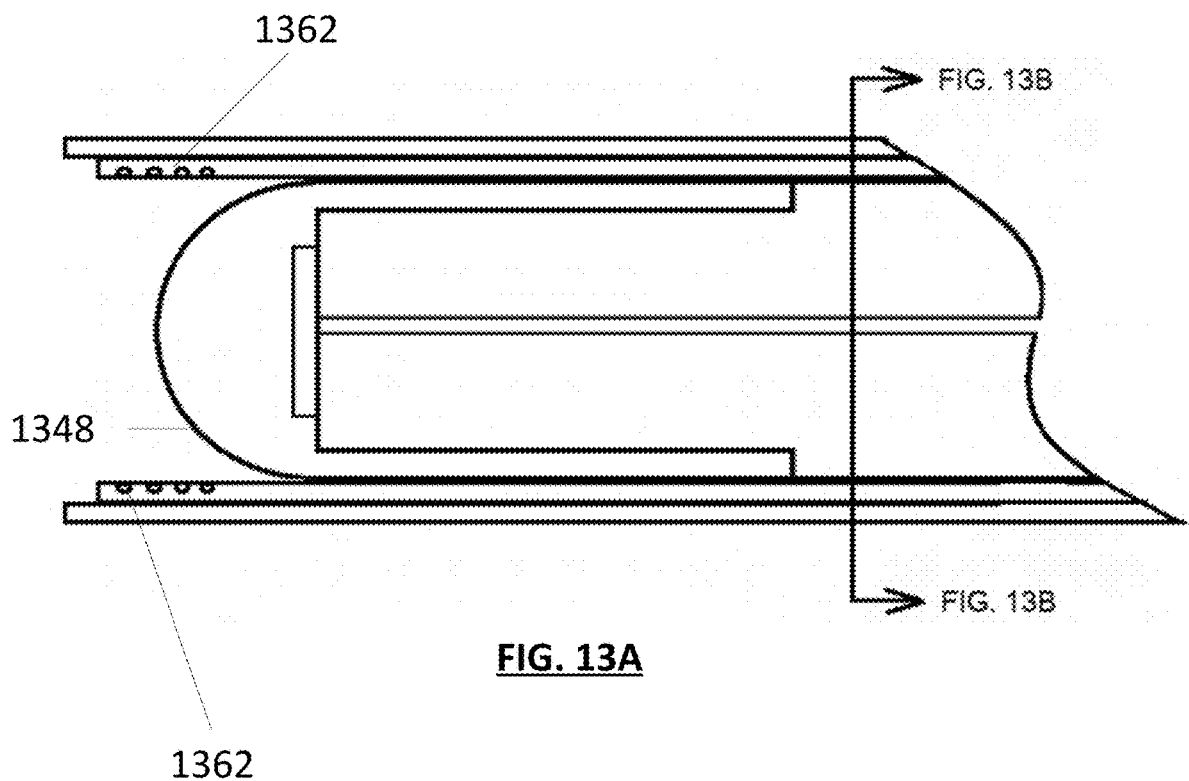
FIGS. 13A-FIG. 13B present a cross sectional and end view, respectively of a further embodiment of a device in accordance with the present disclosure that is configured to facilitate cleaning of a distal tip of the visualization stylet.
Figure 13B:
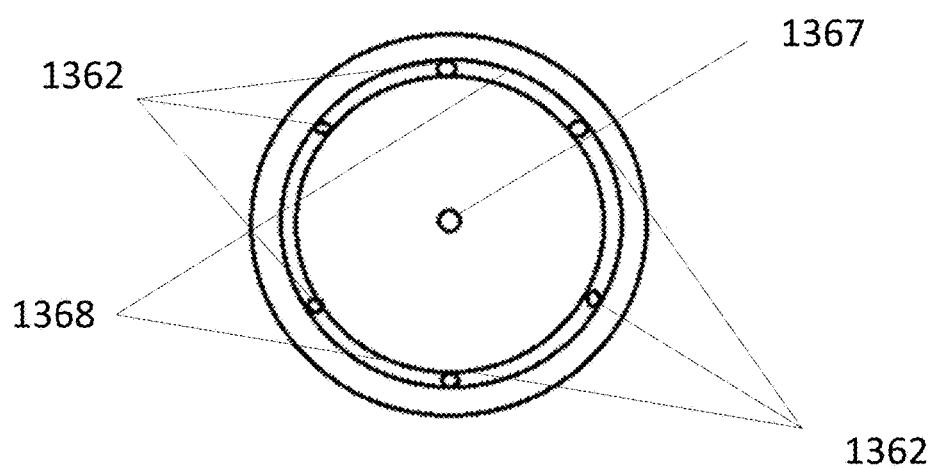

FIGS. 13A-13B illustrate a further embodiment of a visualization Veress needle that incorporates flushing pathways or conduits into the sheath of the needle that surrounds the visualization stylet. As depicted, preferably 3, 4, or 6 longitudinal channels 1362 are provided (such as small hypotubes) that are attached to the inner surface of the sheath (e.g., 220). These tubes 1362 act to evenly space the visualization stylet from the outer sheath, and cooperate with the outer tube and visualization stylet to define longitudinal passages 1368 for the passage of insufflation gas, or simply to reduce friction. As illustrated, the distal tip of tubes 1362 can be sealed, and laser drilled holes can be formed that are transverse to the visualization stylet, such that cleaning fluid directed through the tubes 1362 will be directed transversely across the distal tip of the visualization stylet to clean the lens 1348. Visualization stylet can be moved proximally and distally with respect to the outer sheath when cleaning to facilitate cleaning during a cleaning process.

FIGS. 14A-14C illustrate an embodiment of a visualization Veress needle that can be taken apart to facilitate different procedures. For example, 14A illustrates a distal portion of a Veress needle, such as that illustrated in FIGS. 2A-2C, having an visualization stylet 1406 that is connected to an outer sheath 1402, wherein sheath 1402 is removably connected to a cannula 1404 that provides insufflation gas. After insufflation, portion 1404 can be removed from portion 1402 (e.g., by a screw threaded connection 1409), and a new proximal portion 1408 can be attached to threads 1409 to use the assembly as a laparoscope. If desired, the visualization stylet 1406 can be removed from the assembly of 1402 and 1404 (e.g., by detaching a screw threaded connection). A seal (not shown) inside of component 1402 or 1404 can be provided to prevent the loss of insufflation gas.

FIGS. 15A-15C illustrate a system and method for separating the visualization stylet 1506 from an outer cannula 1504, such as by disconnecting a threaded connection. After the assembly is inserted under visualization into the peritoneum, the visualization stylet can be removed, if desired, leaving the outer sheath in place as a cannula. Or, the outer sheath can be removed, permitting an extension 1508 to be attached to visualization stylet 1506 to effectively use visualization stylet 1506 as a laparoscope. If the visualization stylet is removed, a seal (not shown) can be provided within the body of the cannula 1504 to prevent undue loss of insufflation gas and to maintain pressure in the peritoneum. Visualization stylet can be removed, for example, to remove the lens cap (e.g, 148 et. seq.), permitting the visualization stylet to be reintroduced without the lens cap. In a further embodiment of a method, the lens is hinged to the end of the visualization stylet and can swing out of the way by actuating an actuator.

FIGS. 16A-16C illustrate a further system and method for separating a visualization stylet from an outer cannula that is used to insufflate the peritoneum. The outer cannula includes an insufflation port to receive an insufflation gas input. After the assembly is inserted under direct visualization into the peritoneum in FIG. 16A, the peritoneum can be insufflated, and the visualization stylet can be removed as indicated in FIG. 16B. The inner stylet can include a CMOS chip at its distal end as discussed elsewhere herein that can be covered by a removable distal cap or cover. The removable distal cap or cover can have a sharpened tip or a blunt dissection tip of any desired shape (e.g., conical, pyramidal, etc.) and any additional features that are desired (e.g., ridges or wings or tabs extending outwardly from the removable tip). The tip can thus be removed, and the inner stylet can be replaced into the outer cannula to perform an illumination and/or visualization function. Removal of the tip can be helpful as the tip can become obscured during the initial insertion process. If desired, a different tip can be added to re-cover the CMOS chip, or the CMOS chip can have a lens that is covered by the removable distal tip. The outer cannula can continue to direct carbon dioxide into the peritoneum.

In accordance with another embodiment, the Veress needle is inserted as set forth above under direct visualization. The outer cannula is removed, leaving the inner cannula in place. Then, a second, larger cannula (e.g., having a 5 mm or 10 mm diameter passage, and optionally having an insufflation port) is slid over the inner visualization stylet to dilate the tissue radially outwardly. The visualization stylet can be left in place, or it too can be removed so that a further instrument can be introduced through the newly placed cannula. For example, a larger scope with a larger light source and photodetector array can be inserted to provide improved imaging. Advantageously, this permits entry into the peritoneum under direct visualization using a small instrument, and permits insertion of a much larger trocar without need for an obturator. This can be very important, as there are many documented instances where surgeons have attempted to insert an obturator with a larger trocar in the first instance, resulting in damaging internal structures such as bowels, or in severe cases, the abdominal aorta, resulting in death of the patient. As will be appreciated, trocars that are used and slid over the inner stylet preferably include outer ribs to prevent undesirable axial trocar movement during the procedure. In accordance with further embodiments, the outer sleeves of the insufflation needle disclosed herein can be blunted or dulled, and instead a relatively sharper tip can be provided on the inner visualization stylet. In this instance, a minimal spring mechanism, or no spring mechanism can be used, and the tip of the visualization stylet, while sharper, need not be extremely sharp because of its small diameter. These aspects can be applied to any embodiment of this disclosure.

It will be appreciated that one or more of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the present disclosure.

What is claimed is:

1. A method of using an insufflation needle assembly, comprising:
 providing an insufflation needle assembly comprising:
  an outer assembly including an insufflation input port and a hollow distally extending needle, the hollow distally extending needle having a distal end and a proximal end, wherein the outer assembly forms a conduit to pass at least one of insufflation gas and instruments therethrough; and
  a removable visualization stylet having a proximal end and a distal end, said visualization stylet being slidably disposed within the conduit wherein the outer assembly acts as a sheath that at least partially covers the removable visualization stylet along its length, and further wherein:

i) the outer assembly and removable visualization stylet can be coupled together to permit them to be advanced through tissue as a single structural unit;

ii) a distal end region of the visualization stylet includes an electronic photodetector chip mounted thereon having a distally facing surface to detect incoming light traveling along a proximal direction;

iii) the visualization stylet further includes a light source to project light beyond the electronic photodetector chip in a distal direction to provide direct illumination; and iv) light originating from the light source is reflected back to the electronic photodetector chip when the apparatus is traversing through tissue;

creating an incision in skin of an abdomen of a subject;

advancing a distal end of the insufflation needle assembly into the incision and through successive layers of an abdominal wall of the subject while viewing tissue being advanced through by way of the removable visualization stylet in real time, the removable visualization stylet being configured to view in a distal direction;

stopping advancing the distal end of the insufflation needle assembly upon observing the visualization stylet extending distally with respect to the hollow distally extending needle indicating that an abdominal cavity of the subject has been reached; and removing the removable visualization stylet from the outer assembly, leaving the outer assembly in place in the patient.

2. The method of claim 1, further comprising insufflating the peritoneum through the insufflation needle assembly.

3. The method of claim 2, further comprising:

removing a distal cover from the removable visualization stylet;

reinserting the removable visualization stylet through the outer assembly;

illuminating tissue inside the peritoneum using the removable visualization stylet; and visually observing the tissue inside the peritoneum by way of the electronic photodetector chip.

4. A method as recited in claim 2, wherein insufflating the peritoneum through the outer assembly includes withdrawing the removable visualization stylet proximally with respect to the outer assembly to clear a flow channel through the outer assembly for insufflation gas, and injecting gas through the outer assembly.

\* \* \* \* \*